(12) United States Patent
Gustavsson et al.

(10) Patent No.: US 10,099,032 B2
(45) Date of Patent: Oct. 16, 2018

(54) CATHETER WITH INTEGRATED INSERTION AID

(71) Applicant: DENTSPLY IH AB, Molndal (SE)

(72) Inventors: Evelina Gustavsson, Onsala (SE); Daniel Nestenborg, Västra Frölunda (SE)

(73) Assignee: DENTSPLY IH AB, Mölndal (SE)

( * ) Notice: Subject to any disclaimer, the term of this patent is extended or adjusted under 35 U.S.C. 154(b) by 513 days.

(21) Appl. No.: 14/574,494

(22) Filed: Dec. 18, 2014

(65) Prior Publication Data

US 2015/0112314 A1    Apr. 23, 2015

Related U.S. Application Data

(63) Continuation-in-part of application No. 13/331,560, filed on Dec. 20, 2011, now abandoned.

(30) Foreign Application Priority Data

Dec. 30, 2010 (EP) .................................... 10197422

(51) Int. Cl.
*A61M 25/00* (2006.01)
*B29C 45/26* (2006.01)
(Continued)

(52) U.S. Cl.
CPC ....... *A61M 25/0017* (2013.01); *B29C 45/261* (2013.01); *A61M 25/0009* (2013.01);
(Continued)

(58) Field of Classification Search
CPC .. B29C 45/261; B29C 45/16; A61M 25/0009; A61M 25/0017; A61M 25/0111; A61M 25/0014; A61M 25/0097
See application file for complete search history.

(56) References Cited

U.S. PATENT DOCUMENTS 3,470,604 A    10/1969    Zenick
3,613,684 A    10/1971    Sheridan
(Continued)

FOREIGN PATENT DOCUMENTS

CH    414067    5/1966
CN    1281198    10/2006
(Continued)

OTHER PUBLICATIONS

European Search Report, Application No. 10197422.8-1526, Published Jun. 14, 2011.
(Continued)

*Primary Examiner* — Adam Marcetich
*Assistant Examiner* — Jessica Arble
(74) *Attorney, Agent, or Firm* — Perkins Coie LLP

(57) ABSTRACT

A catheter is disclosed that includes an elongated shaft, an insertable end formed in or connected to one end of the elongated shaft, and a discharge end formed in or connected to the opposite end of the elongated shaft. Further, the catheter includes an insertion aid that at least partly encircles the discharge end, and is integrally and releasably connected to the discharge end. The catheter can be easily produced, and at the same time, the insertion aid may easily be removed for use as an insertion aid when using the catheter.

15 Claims, 2 Drawing Sheets

(51) Int. Cl.
*A61M 25/01* (2006.01)
*B29C 45/16* (2006.01)
*B29L 31/00* (2006.01)

(52) U.S. Cl.
CPC .......... *A61M 25/0111* (2013.01); *B29C 45/16* (2013.01); *B29L 2031/7542* (2013.01); *Y10T 29/49826* (2015.01)

(56) References Cited

U.S. PATENT DOCUMENTS

| | | | |
|---|---|---|---|
| 4,468,146 A | 8/1984 | Tabachnik | |
| 4,643,389 A | 2/1987 | Elson et al. | |
| 4,735,618 A | 4/1988 | Hagen | |
| 4,840,619 A | 6/1989 | Hughes | |
| 4,846,808 A | 7/1989 | Haber et al. | |
| 4,921,479 A | 5/1990 | Grayzel | |
| 5,069,669 A | 12/1991 | Kole | |
| 5,084,032 A | 1/1992 | Kornberg et al. | |
| 5,125,904 A | 6/1992 | Lee | |
| 5,219,339 A | 6/1993 | Saito | |
| 5,242,428 A | 9/1993 | Palestrant | |
| 5,279,581 A | 1/1994 | Firth et al. | |
| 5,295,972 A | 3/1994 | Mischenko | |
| 5,330,438 A | 7/1994 | Gollobin et al. | |
| 5,368,575 A | 11/1994 | Chang | |
| 5,398,947 A | 3/1995 | Cook | |
| 5,441,504 A | 8/1995 | Pohndorf et al. | |
| 5,800,399 A | 9/1998 | Bogert et al. | |
| 5,827,239 A | 10/1998 | Dillon et al. | |
| 6,149,332 A | 11/2000 | Huang | |
| 6,299,589 B1* | 10/2001 | Utterberg | A61M 1/3621 604/28 |
| 6,355,004 B1* | 3/2002 | Pedersen | A61F 5/44 600/581 |
| 6,554,807 B2 | 4/2003 | Gollobin | |
| 6,613,014 B1 | 9/2003 | Chi | |
| 6,613,041 B1 | 9/2003 | Chi | |
| 7,476,223 B2 | 1/2009 | McBride | |
| 2002/0002872 A1 | 1/2002 | Wessel | |
| 2003/0229297 A1 | 12/2003 | Christensen et al. | |
| 2004/0020335 A1 | 2/2004 | Chen | |
| 2004/0068844 A1 | 4/2004 | Lumpkin | |
| 2004/0186445 A1 | 9/2004 | Raulerson et al. | |
| 2004/0186447 A1 | 9/2004 | Mori | |
| 2005/0015076 A1 | 1/2005 | Giebmeyer et al. | |
| 2005/0015934 A1 | 1/2005 | Hu | |
| 2005/0267487 A1 | 12/2005 | Christensen et al. | |
| 2006/0236522 A1 | 10/2006 | Lin | |
| 2007/0066963 A1* | 3/2007 | Tanghoj | A61M 25/0017 604/523 |
| 2007/0239118 A1 | 10/2007 | Ono et al. | |
| 2008/0027414 A1* | 1/2008 | Tanghoj | A61F 5/44 604/523 |
| 2008/0097362 A1 | 4/2008 | Mosler et al. | |
| 2009/0139380 A1 | 6/2009 | Pyatt | |
| 2009/0208368 A1 | 8/2009 | Waldrep et al. | |
| 2010/0241083 A1 | 9/2010 | Fisher et al. | |
| 2010/0286664 A1 | 11/2010 | Haslinger | |
| 2011/0060317 A1* | 3/2011 | Frojd | A61M 25/0009 604/544 |
| 2011/0114520 A1 | 5/2011 | Matthison-hansen | |
| 2011/0123253 A1 | 5/2011 | Matsui | |
| 2011/0162490 A1 | 7/2011 | Chang | |
| 2011/0301551 A1 | 12/2011 | Koehler et al. | |
| 2012/0073086 A1 | 3/2012 | Rarick | |
| 2012/0239070 A1 | 9/2012 | Wijay | |
| 2013/0038579 A1 | 2/2013 | Boyd et al. | |
| 2014/0066905 A1 | 3/2014 | Young | |

FOREIGN PATENT DOCUMENTS

| | | |
|---|---|---|
| EP | 0217771 B1 | 12/1991 |
| EP | 1504870 | 2/2005 |
| EP | 1131022 B1 | 8/2005 |
| EP | 2106821 A1 | 10/2009 |
| EP | 2292294 A1 | 3/2011 |
| GB | 322426 | 12/1929 |
| SU | 1165412 | 7/1985 |
| WO | 200030575 | 6/2000 |
| WO | 2000030575 A1 | 6/2000 |
| WO | 2000040284 A1 | 7/2000 |
| WO | 2001017599 | 3/2001 |
| WO | 2004089454 A1 | 10/2001 |
| WO | 2011026929 A1 | 3/2011 |

OTHER PUBLICATIONS

Chinese Office Action for Chinese Patent Application No. 201180062415.6, dated May 26, 2015, with translation (18 pages).
Chinese Office Action for Chinese Patent Application No. 201180062415.6, dated Sep. 30, 2015, with translation (12 pages).
European Search Report, Application No. 12158070.8, Published Aug. 16, 2012.

\* cited by examiner

CATHETER WITH INTEGRATED INSERTION AID

TECHNICAL FIELD OF THE INVENTION

The present invention is related to a catheter, and in particular a urinary catheter, with an insertion aid to facilitate handling of the catheter.

BACKGROUND

Catheters, such as urinary catheters, and in particular catheters having hydrophilic coatings, are relatively difficult to handle, since the surface before application is very slippery. Further, direct contact with the insertable part of the catheter should preferably be avoided, in order to avoid contamination of the catheter, and thereby minimize the risk of urinary tract infections. Still further, many users of intermittent urinary catheterization are disabled or have poor dexterity for other reasons, and consequently, there is also a need for means for making insertion of catheters easier and cleaner/safer.

To overcome these problems, many alternative insertion aids have been proposed during the last years. For example, EP 1131 022 discloses an applicator which is formed as an integrated and detachable hose member arranged in the catheter package in which the catheter is arranged. However, as a consequence, the catheter package becomes relatively complicated and costly, and also, the operation of this catheter assembly is relatively cumbersome.

Further, EP 2 106 821 discloses a catheter assembly in which an insertion aid is arranged as a tubular part arranged over the connector part of the catheter. Upon use, the tubular insertion aid may easily be loosened from its position on the connector, and moved along the catheter shaft. However, this solution is also relatively complicated and costly, since it requires the use of multiple components which are to be assembled together, and does consequently not lend itself for fully automated production.

There is therefore still a need for a catheter assembly having an insertion aid which is easier to use and/or easier and more cost-efficient to produce.

SUMMARY OF THE INVENTION

There is therefore an object of the present invention to provide a catheter and a method of manufacture that at least partly overcome the above-discussed problems of the prior art.

This object is achieved by means of a catheter and a method for manufacture according to the enclosed claims.

According to a first aspect of the invention there is provided a catheter comprising an elongate shaft, an insertable end formed in or connected to one end of said elongate shaft, and a discharge end formed in or connected to the opposite end of said elongate shaft, wherein said catheter further comprises an insertion aid at least partly encircling said discharge end, and being integrally and releasably connected to said discharge end.

Hereby, the insertion aid is formed as an integrated and unitary part of the catheter, which can be produced concurrently with the reminder of the catheter in an automated procedure. Further, the insertion aid will always be kept securely in place before it is removed and used as an insertion aid. At the same time, if the user does not need an insertion aid, the insertion aid can be allowed to remain in its non-released state during the entire use. Accordingly, the insertion aid is released and activated if or when it is needed, but will otherwise function as an integral part of the connector end of the catheter.

The insertion aid is further easy to remove, and thereafter to move along the length of the elongate shaft, thereby facilitating contamination free handling of the catheter, which reduces the risk of urinary tract infections and the like. Preferably, the discharge end and the insertion aid are formed and connected by means of injection molding. Hereby, these parts are easily produced and connected together. Most preferably, the discharge end and the insertion aid are formed and connected by means of injection molding in a single molding cycle. However, alternatively, the discharge end and the insertion aid may be formed and connected by means of injection molding in at least two separate molding cycles, and preferably without opening the mold(s). This is preferred if there is, for example, a need for different materials in the insertion aid and the discharge end of the catheter. If two separate molding cycles are used, the integration of the discharge end and the insertion aid may still be directly molded together. However, alternatively, it is possible to use a two-step molding process in which the discharge end and the insertion aid are formed in two separate molding cycles, preferably without opening the molds, and mechanically interconnected within the molding apparatus. The connection may in this case be accomplished by, for example, a bayonet joint.

By molding cycle is here meant the sequence of events during the injection mold of a component or part, including injecting and solidifying of a material. Optionally, and depending on the circumstances, a molding cycle may also include closing the mold around a mold cavity, and, once the part is sufficiently cool, opening the mold and ejecting the part. Thus, when several molding cycles are used without opening of the mold(s), this corresponds to several injection steps within a single overall molding cycle.

The discharge end and the insertion aid are preferably connected by means of at least one breakable connection arms extending between the discharge end and the insertion aid. Hereby, the breakable connection arms securely maintain the insertion aid and the discharge end connected during production assembly, storage and before the intended use. When the insertion aid is to be used as an insertion aid, the insertion aid may easily be broken off, and removed from its initial position. For example, the removal may be accomplished by means of applying a force in a certain direction and exceeding a certain value. Most preferably, the arms have a longer extension in the length direction of the catheter than in the circumferential direction of the catheter. Hereby, the insertion aid is easy to remove by applying a rotational force to the insertion aid in relation to the discharge end, and at the same time, the insertion aid is not involuntarily removed during ordinary handling of the catheter, where forces are normally applied in the axial direction. Further, the connection between the insertion aid and the discharge end is preferably arranged to be released upon a rotational movement of the insertion aid in relation to the discharge end.

The insertion aid preferably comprises a tubular part arranged at least partly over the discharge end.

In a preferred embodiment, the discharge end forms an inwardly funnel shaped end, whereby the discharge opening increases in cross-sectional dimensions in a direction away from the insertable end, and an outwardly facing, cylindrical surface having an essentially uniform diameter. Hereby, it is easy to provide the connection between the discharge end and the insertion aid, and at the same time, the normal connectability of the catheter in the inwardly tapering opening to external tubing, such as a tube leading to a urine collection bag can be obtained in a normal way.

The discharge end and the insertion aid are preferably formed by the same material. Further, the elongate shaft and the tip portion may also be of the same material. Alternatively, the various components of the catheter may be of different materials. For example, the discharge end and the insertion aid may be formed by two different materials. Other parts of the catheter, such as the tip portion, may optionally also be formed by a different material than the rest of the elongate shaft.

The at least one material may be any thermoplastic and/or thermosetting plastic materials which are useable for providing sufficient strength and flexibility for the intended use.

In order to further facilitate insertion of the catheter, the elongate shaft may comprise a hydrophilic material at the surface, said hydrophilic material providing a low-friction character to the catheter surface when wetted. For example, the elongate shaft can be made essentially entirely of a hydrophilic material. Alternatively, the elongate shaft may be provided with a hydrophilic surface coating.

According to another aspect of the invention there is provided a method of producing a catheter comprising the steps: providing or forming an elongate shaft having an insertable end formed in or connected to one end of the elongate shaft;

forming a discharge end formed in or connected to the opposite end of said elongate shaft; and forming an insertion aid at least partly encircling said discharge end, and being integrally and releasably connected to said discharge end.

By means of this aspect of the invention, similar advantages and possible additional features as discussed above in relation to the first aspect of the invention are obtainable.

In a preferred embodiment, the discharge end and the insertion aid are formed by injection molding, using one or several materials. It is further preferred that the entire catheter is formed by injection molding, using one or several materials.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
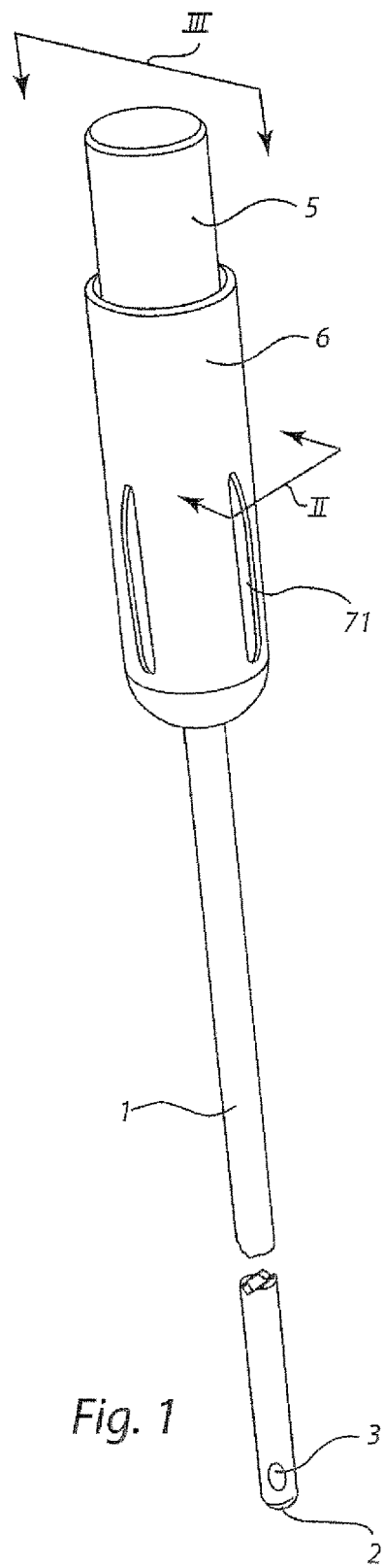
FIG. 1 is a side view in perspective of a catheter according to an embodiment of the present invention.

In the following detailed description, preferred embodiments of the present invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

The following discussion is in particular concerned with hydrophilic urinary catheters for intermittent use. However, the invention can also be used in relation to other types of urinary catheters, or other types of catheters in general.

Figure 2:
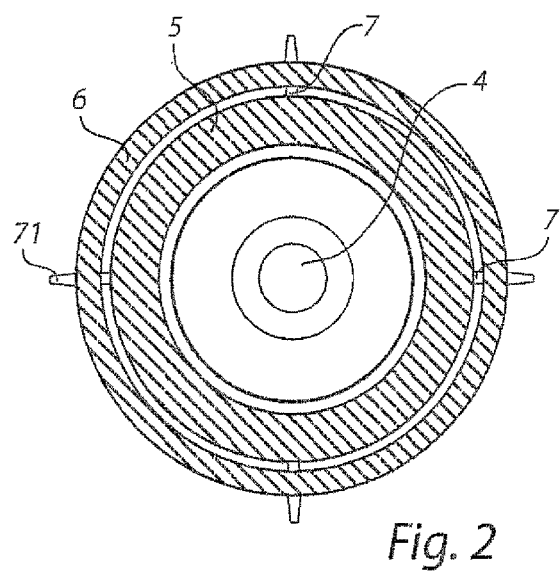
FIG. 2 is a cross-sectional view of the catheter of FIG. 1 in plane II.
Figure 3:
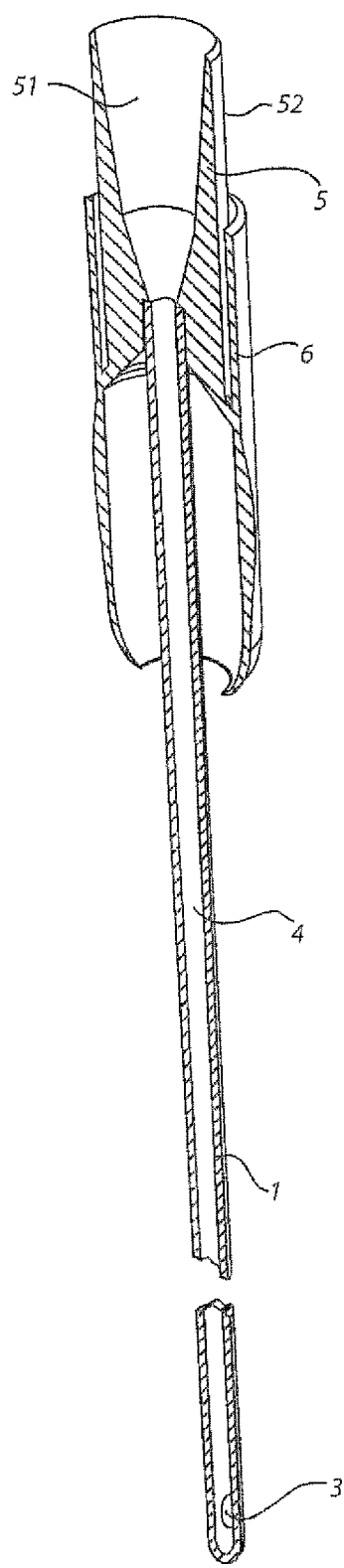
FIG. 3 is a cross-sectional view of the catheter of FIG. 1 in plane III.

A urinary catheter according to a preferred embodiment is illustrated in FIGS. 1-3. The catheter comprises an elongate shaft 1 with an insertion end 2. The insertion end 2 is preferably provided with one or several openings 3, in fluid communication with an internal lumen 4 of the catheter.

The catheter further comprises a discharge end 5 with an integrally formed and connected insertion aid 6.

As is best seen in FIG. 3, the discharge end 5 is preferably arranged with an inwardly tapering inner surface 51, arranged to be connectable to a frusto-conical connection to external tubing or a urine collection bag. The discharge end is further preferably arranged with a cylindrical outer or outwardly facing surface 52. As shown in the drawings such as FIG. 3, inner surface 51 is tapered as described but outward surface 52 is essentially or substantially uniform in diameter, again in a preferred embodiment. However, alternatively, the outer surface may have other shapes, such as having a tapering cross-section, a non-circular circumference, or the like.

The insertion aid 6 is preferably formed as a tubular part, with an inner cross-sectional dimension slightly larger than the corresponding outer surface of the discharge end. However, the insertion aid may also incorporate a slit opening extending over part of the axial length of the tubular part, or even extending over the entire axial length. Further, the insertion aid may have cross-sectional shapes other than circular.

The insertion aid 6 is releasably connected to the discharge end, so that it may be released by will, e.g. by applying a certain force in a certain direction. The released insertion aid may then be moved along the elongate shaft, for aiding during catheterization.

The insertion aid is preferably sufficiently flexible to be compressed, e.g. by applying a pressure between the thumb and the index finger, over the elongate shaft. Sufficient flexibility of the insertion aid may be accomplished by forming it by a sufficiently flexible material, and/or by having a sufficiently narrow thickness. Further, the thickness may vary over the tubular part, thereby making some parts more flexible than others. Preferably, the tubular part has a Shore A hardness in the range 60-80.

The connection between the insertion aid and the discharge end is preferably formed by means of one or several breakable connection arms 7 extending between the discharge end and the insertion aid. Preferably, at least two, and most preferably three or four connection arms 7 are provided. The plurality of connection arms are preferably evenly distributed around the circumference of the discharge end.

Preferably, the arms 7 have a longer extension in the length direction of the catheter than in the circumferential direction of the catheter. Hereby, the resistance to axial forces are greater than the resistance to rotational forces.

In order to further facilitate removal of the insertion aid, gripping means 71, such as protruding portions, may be arranged on the outer surface of the insertion aid.

The catheter may be of any size suitable for catheterization. For use by female users the elongate shaft preferably has a length in the range of 5-20 cm, such as in the size of 15 cm. Hereby, a very compact and discreet catheter is obtained. For male users, the elongate shaft preferably has a length in the range 18-45 cm, such as in the size of 40 cm.

Preferably, the discharge end and the insertion aid are formed and connected by means of injection molding. Most preferably, the discharge end and the insertion aid are formed and connected by means of injection molding in a single molding cycle. However, alternatively, the discharge end and the insertion aid may be formed and connected by means of injection molding in at least two separate molding cycles. This is preferred if there is, for example, a need for different materials in the insertion aid and the discharge end of the catheter. If two separate molding cycles are used, the integration of the discharge end and the insertion aid may still be directly molded together. However, alternatively, it is possible to use a two-step molding process in which the discharge end and the insertion aid are formed in two separate molding cycles, and mechanically interconnected within the molding apparatus. Hereby, the insertion aid and the discharge end may be formed at a distance from each other, and then moved together while still within the molds after sufficiently solidified. The connection may in this case be accomplished by a bayonet joint.

The discharge end and the insertion aid are preferably formed by the same material. Further, the elongate shaft and the tip portion may also be of the same material. Alternatively, the various components of the catheter may be of different materials. For example, the discharge end and the insertion aid may be formed by two different materials.

The at least one material may be any thermoplastic and/or thermosetting plastic materials which are useable for providing sufficient strength and flexibility for the intended use. For example, the material may be one or several of: a polymer material, such as polyurethanes, thermoplastic rubbers, polyvinylchloride, other vinyl polymers, polyesters, polyether block amid, polypropene, polyethen polyamide and styren-ethen/butadiene-styren co-polymer and polyacrylates. The material may also be a polymer blend comprising a polyolefin and a composition having molecules with active hydrogen groups, and preferably a composition having molecules with active hydrogen groups. The polyolefin can comprise at least one polymer selected from the group: polyethene, polypropene, and styrene block copolymer (SCBS). The composition having molecules with active hydrogen groups can be a polymer having active hydrogen groups bound to the polymer via nitrogen, such as polyamide or polyurethane.

In order to further facilitate insertion of the catheter, the elongate shaft may comprise a hydrophilic material at the surface, said hydrophilic material providing a low-friction character to the catheter surface when wetted. For example, the elongate shaft can be made essentially entirely of a hydrophilic material. Alternatively, the elongate shaft may be provided with a hydrophilic surface coating.

The hydrophilic material may be polyvinyl pyrrolidone (PVP), but many other types of hydrophilic coatings are known in the art, and may be used in the context of the present invention. The hydrophilic coating provides a low-friction character to the catheter when wetted, thereby facilitating insertion of the catheter into the urethra, and reducing the risk of pain etc.

More specifically, the hydrophilic material may comprise material(s) selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone. In case the hydrophilic material is arranged as a coating, the coating preferably forms a polyurea network, whereby said polyurea network forms a covalent bond to said active hydrogen groups in the substrate. Alternatively, the hydrophilic coating may form an ester bond or an epoxy bond to said active hydrogen groups in the substrate.

The coating may also comprise an osmolality-increasing compound, as is e.g. taught in EP 0 217 771.

The above-discussed and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements.

What is claimed is:

1. A catheter comprising an elongate shaft, an insertable end formed in or connected to one end of said elongate shaft, and a discharge end formed in or connected to an opposite end of said elongate shaft, wherein said catheter further comprises an insertion aid at least partly encircling said discharge end, and being integrally and releasably-connected to said discharge end to allow said insertion aid to be removed from said discharge end during use of said catheter; wherein the discharge end and the insertion aid are formed and connected by injection molding, and wherein the discharge end and the insertion aid are connected by one or more breakable connection arms extending between the discharge end and the insertion aid.

2. The catheter of claim 1, wherein the discharge end and the insertion aid are formed and connected by means of injection molding in a single molding cycle.

3. The catheter of claim 1, wherein the discharge end and the insertion aid are formed and connected by means of injection molding in at least two separate molding cycles, without opening injection molds.

4. The catheter of claim 3, wherein the discharge end and the insertion aid are formed in two separate molding cycles without opening the molds, and mechanically interconnected within a molding apparatus.

5. The catheter of claim 1, wherein the arms have a longer extension in an axial direction of the catheter than in a circumferential direction of the catheter.

6. The catheter of claim 1, wherein the insertion aid comprises a tubular part arranged at least partly over said discharge end.

7. The catheter of claim 1, wherein the discharge end and the insertion aid are formed by same material.

8. The catheter of claim 1, wherein the discharge end and the insertion aid are formed by two different materials.

9. The catheter of claim 1, wherein a connection between the insertion aid and the discharge end is arranged to be released upon a rotational movement of the insertion aid in relation to the discharge end.

10. The catheter of claim 1, wherein the discharge end forms an inwardly funnel shaped end, whereby the discharge opening increases in cross-sectional dimensions in a direction away from the insertable end, and an outward surface having an essentially uniform diameter.

11. The catheter of claim 1, comprising at least two breakable connection arms, wherein the at least two breakable arms are evenly distributed around the circumference of the discharge end.

12. The catheter of claim 1, wherein at least one of the one or more breakable connection arms has a longer extension in a direction along the length of the catheter than along circumference of the catheter, whereby resistance to axial forces are greater than resistance to rotational forces.

13. A method of producing a catheter comprising the steps: providing or forming an elongated shaft having an insertable end formed in or connected to one end of the elongated shaft; forming a discharge end formed in or connected to an end opposite to said insertable end of said elongate shaft; and forming an insertion aid at least partly encircling said discharge end, and being integrally and releasably connected to said discharge end to allow said insertion aid to be removed from said discharge end during use of said catheter; wherein the discharge end and the insertion aid are formed and connected by injection molding, and wherein the discharge end and the insertion aid are connected by one or more breakable connection arms extending between the discharge end and the insertion aid.

14. The method of claim 13, wherein the entire catheter is formed by injection molding.

15. The method of claim 13, wherein the discharge end forms an inwardly funnel shaped end that includes opening that increases in cross-sectional dimensions in a direction away from the insertable end, and the discharge end includes an outward surface having an essentially uniform diameter.

* * * * *